United States Patent
Stock et al.

(10) Patent No.: US 7,499,154 B2
(45) Date of Patent: Mar. 3, 2009

(54) READHEAD FOR OPTICAL INSPECTION APPARATUS

(75) Inventors: Nicholas T. Stock, Govilon (GB); Gary D. Ross, Monmouth (GB); David J. Ledden, Medway, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 339 days.

(21) Appl. No.: 10/556,299

(22) PCT Filed: Jun. 3, 2004

(86) PCT No.: PCT/US2004/018233

§ 371 (c)(1), (2), (4) Date: Nov. 11, 2005

(87) PCT Pub. No.: WO2004/109263

PCT Pub. Date: Dec. 16, 2004

(65) Prior Publication Data

US 2007/0064220 A1    Mar. 22, 2007

Related U.S. Application Data

(60) Provisional application No. 60/475,288, filed on Jun. 3, 2003.

(51) Int. Cl.
    G01N 21/00    (2006.01)
(52) U.S. Cl. .................. 356/73; 356/317; 356/445; 356/416
(58) Field of Classification Search .............. 356/218, 356/402, 417, 317, 318, 445–448, 73, 51; 250/461.1, 365, 372, 504 R; 600/312, 319, 600/317, 347, 365, 368
    See application file for complete search history.

(56) References Cited

U.S. PATENT DOCUMENTS 5,260,584 A    11/1993    Popson et al.

(Continued)

FOREIGN PATENT DOCUMENTS

EP    0 866 329 A2    9/1998

(Continued)

Primary Examiner—L. G Lauchman
(74) Attorney, Agent, or Firm—Noam R. Pollack; McDermott, Will & Emery

(57) ABSTRACT

A readhead for illuminating a sample carrier and receiving light from the sample carrier, including a housing for receiving a sample carrier, an array of light sources mounted within the housing in a fixed position relative to the sample carrier, and including first and second light-emitting diodes for emitting substantially monochromatic light of a two different wavelengths, a light guide mounted in the housing between the light-emitting diodes and the sample carrier, and a light detector coupled to receive light from the sample carrier. The readhead also includes a light source for directing excitation light of a predetermined wavelength to the sample carrier, and a light filter positioned between the sample carrier and the light detector and adapted to prevent passage therethrough of the excitation light. The readhead allows both fluorescence spectroscopy and reflectance spectroscopy to be conducted on the sample carrier.

37 Claims, 3 Drawing Sheets

U.S. PATENT DOCUMENTS

| | | | |
|---|---|---|---|
| 5,869,272 A * | 2/1999 | Bogart et al. | 435/7.32 |
| 5,877,863 A * | 3/1999 | Ross et al. | 356/445 |
| 6,122,042 A * | 9/2000 | Wunderman et al. | 356/73 |
| 6,278,521 B1 * | 8/2001 | Jablonski et al. | 356/402 |
| 6,445,451 B1 * | 9/2002 | Douglas-Hamilton et al. | 356/425 |
| 6,492,133 B1 * | 12/2002 | Wickert et al. | 435/34 |
| 6,704,587 B1 * | 3/2004 | Kumar et al. | 600/316 |
| 7,139,068 B2 * | 11/2006 | Jung et al. | 356/73 |

FOREIGN PATENT DOCUMENTS

| | | |
|---|---|---|
| EP | 1 293 926 A2 | 3/2003 |
| WO | WO 97/20495 | 6/1997 |

\* cited by examiner

READHEAD FOR OPTICAL INSPECTION APPARATUS

CROSS-REFERENCE TO RELATED APPLICATIONS

The present application claims priority from provisional U.S. patent application Ser. No. 60/475,288, filed Jun. 3, 2003, which is incorporated herein by reference in its entirety.

FIELD OF THE DISCLOSURE

The present disclosure relates to an apparatus and method for optically inspecting a sample of body fluid and, more particularly, to a readhead for use with the apparatus. Even more particularly, the present disclosure relates to a readhead including components for conducting both fluorescence and reflectance spectroscopy.

BACKGROUND OF THE DISCLOSURE

It is useful for various medical diagnostic purposes to utilize a reflectance spectroscope to analyze samples of body fluid, for example, to determine the color of a person's urine or blood. As is known, spectroscopy uses the linear relationship between absorbance and concentration of an absorbing species (Beer's law), to determine the contents of a sample. An unknown concentration of an analyte can be determined by measuring the amount of light that a sample absorbs and applying Beer's law. If the absorptivity coefficient of the analyte is not known, the unknown concentration can be determined using a working curve of absorbance versus concentration derived from standards.

For example, immunoassay is a technology for identifying and quantifying organic and inorganic compounds. Immunoassay uses antibodies that have been developed to bind with a target compound or class of compounds. The technology has been used widely because the antibodies can be highly specific to the target compound or group of compounds and because immunoassay kits are relatively quick and simple to use. Concentrations of analytes are identified through the use of a sensitive colorimetric reaction. The determination of the target analyte's presence is made by comparing the color developed by a sample of unknown concentration with the color formed by the standard containing the analyte at a known concentration. The concentration of the analyte is determined by the intensity of color in the sample. The concentration can be estimated roughly by the naked eye or can be determined more accurately with a reflectance spectroscope.

Reflectance spectroscopy is the study of light as a function of wavelength that has been reflected or scattered from a solid, liquid, or gas. A conventional reflectance spectroscope may determine the color of a liquid sample, such as urine or blood, disposed on a white, non-reactive pad by illuminating the pad and taking a number of reflectance readings from the pad, each having a magnitude relating to a different wavelength of visible light. The color of the sample on the pad may then be determined based upon the relative magnitudes of red, green, blue and infrared reflectance signals. Reagent pads can be provided with different reagents which cause a color change in response to the presence of a certain type of constituent in urine, such as leukocytes (white blood cells) or red blood cells. A reagent strip may have ten or more different types of reagent pads, for example. Immunoassay strips or cassettes may also be used with other types of liquid samples, such as blood.

U.S. Pat. No. 5,654,803, which is assigned to the assignee of the present disclosure, discloses an apparatus and method for determination of non-hemolyzed levels of occult blood in urine using reflectance spectroscopy. The apparatus is provided with a light source for successively illuminating a plurality of different portions of a reagent pad on which a urine sample is disposed, and a detector array for detecting light received from the reagent pad and generating a plurality of reflectance signals in response to light received from a corresponding one of the different portions of the reagent pad. The apparatus is also provided with means for determining whether the magnitude of one of the reflectance signals is substantially different than the magnitude of another of the reflectance signals. Where the body-fluid sample is urine, this capability allows the apparatus to detect the presence of non-hemolyzed levels of occult blood in the urine sample.

U.S. Pat. No. 5,877,863, which is also assigned to the assignee of the present disclosure, shows an optical inspection apparatus for inspecting a liquid sample, such as urine, using reflectance spectroscopy. The apparatus includes a readhead for illuminating a target area substantially uniformly via only a single light-emitting diode for each wavelength of interest and receiving light from the target area so that reagent tests may be performed. The readhead is provided with a housing, first and second light sources mounted in a fixed position relative to the housing, a light guide mounted to receive light from each of the light sources which conveys, when only one of the light sources is illuminated, substantially all of the light from the light source to illuminate a target area substantially uniformly, and a light detector coupled to receive light from the target area. Each of the first and second light sources is composed of only a single light-emitting diode for emitting substantially monochromatic light of a different wavelength.

Fluorescence spectroscopy is the study of light that has been absorbed at one wavelength and re-emitted at a different wavelength (e.g., fluorescent light is re-emitted by a sample of body fluid in response to a light having a specific wavelength, such as ultraviolet light, being directed at the sample). It is useful for various medical diagnostic purposes to use fluorescence detection to analyze samples of body fluid, for example, to determine a level of glucose in a patient's blood or urine, or to determine a pH level of the patient's blood or urine. U.S. Pat. No. 6,232,609 to Snyder et al., for example, shows an apparatus for glucose monitoring. The glucose monitor illuminates a sample with water with ultraviolet excitation light that induces the water and any glucose present in the sample to emit return light that includes Raman scattered light and glucose emission or fluorescence light. The return light is monitored and processed using a predictive regression model to determine the concentration of glucose in the sample. The predictive regression model accounts for nonlinearities between the glucose concentration and intensity of return light within different wavelength bands at a predetermined excitation light energy or the intensity of return light within a predetermined wavelength band at different excitation energy levels. A fiber-optic waveguide is used to guide the excitation light from a laser excitation source to the sample and the return light from the sample to a sensor.

What is still desired is a new and improved apparatus and method for performing tests on a sample of body fluid and, more particularly, to a readhead for use with the apparatus.

Preferably the readhead will include components for conducting both fluorescence spectropy and reflectance spectroscopy.

SUMMARY OF THE DISCLOSURE

The disclosure is directed to exemplary embodiments of a new and improved readhead for a diagnostic instrument for illuminating a sample carrier (e.g., a strip or cassette having a liquid sample) and receiving light from the sample carrier, and that allows both fluorescence spectroscopy and reflectance spectroscopy to be conducted in a simple and convenient manner.

One exemplary embodiment of the readhead includes a housing adapted to be incorporated in the diagnostic instrument and including an illumination chamber for receiving a sample carrier, an array of light sources mounted within the housing in a fixed position relative to the illumination chamber, and including a first light-emitting diode for emitting substantially monochromatic light of a first wavelength and a second light-emitting diode for emitting substantially monochromatic light of a second wavelength substantially different from the first wavelength, a light guide mounted in the housing to receive light from each of the light-emitting diodes, for conveying, when only one of the light-emitting diodes is illuminated, substantially all of the light from the one light-emitting diode to the illumination chamber so that the illumination chamber is illuminated substantially uniformly, and a light detector coupled to receive light from the illumination chamber. These components of the readhead allow reflectance spectroscopy to be conducted on a fluid sample.

The readhead also includes a fluorescence excitation light source for directing excitation light of a predetermined wavelength to the illumination chamber, and a light filter positioned between the illumination chamber and the light detector and adapted to prevent passage therethrough of the excitation light from the fluorescence excitation light source but allow passage of emissive light from a sample carrier in the illumination chamber having a wavelength different from the predetermined wavelength of the excitation light. These components of the readhead allow fluorescence spectroscopy to be conducted on a fluid sample.

Additional aspects and advantages of the present disclosure will become readily apparent to those skilled in this art from the following detailed description, wherein only exemplary embodiments of the present disclosure are shown and described, simply by way of illustration of the best mode contemplated for carrying out the present disclosure. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

Reference is made to the attached drawings, wherein elements having the same reference character designations represent like elements throughout, and wherein.

DETAILED DESCRIPTION OF EXEMPLARY EMBODIMENTS

Figure 1:
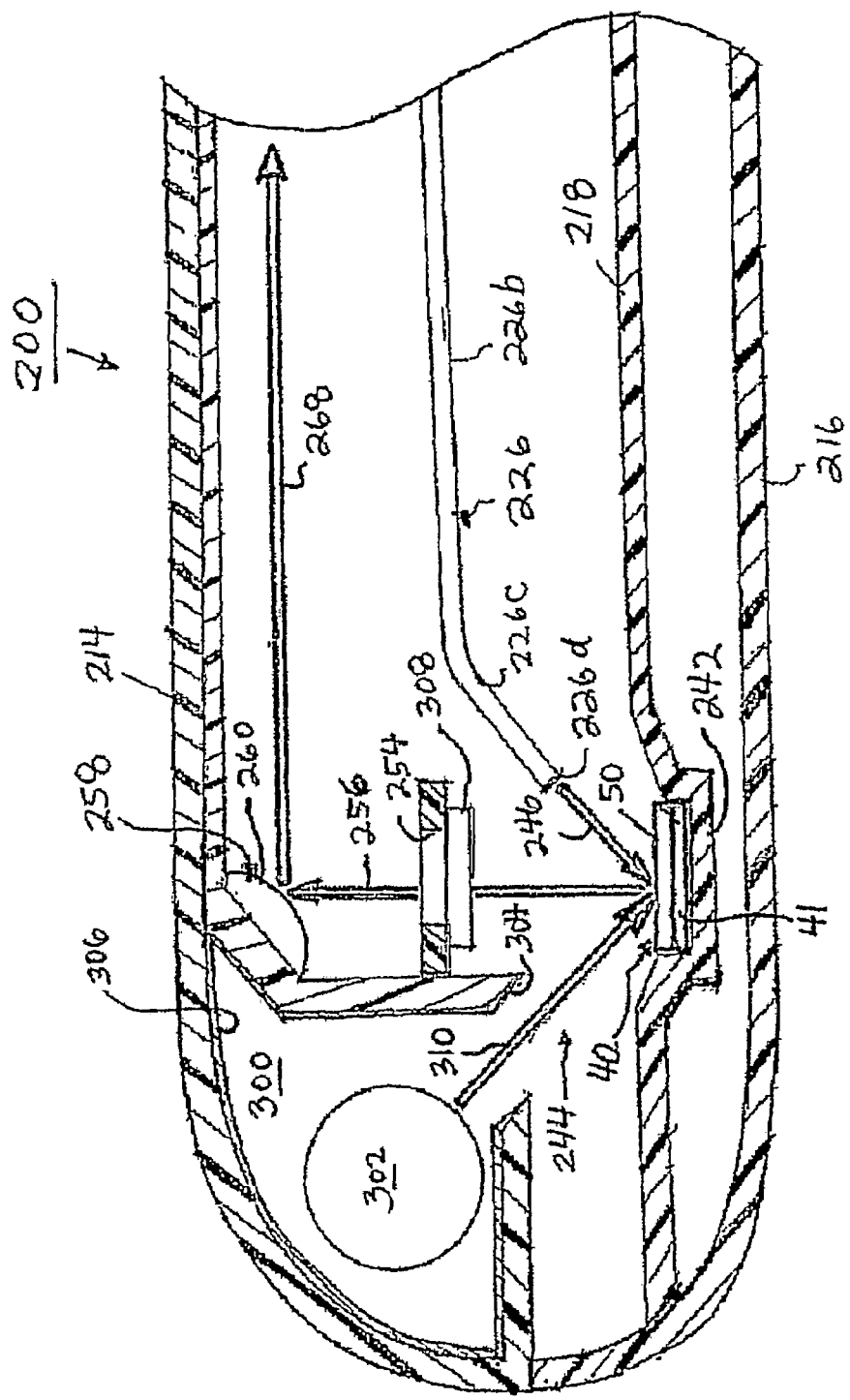
FIG. 1 is a side sectional view of a portion of an exemplary embodiment of a readhead constructed in accordance with the present disclosure, for use as part of a medical diagnostic optical inspection apparatus and which is adapted to perform both fluorescence spectroscopy and reflectance spectroscopy on a body fluid sample.

FIG. 1 shows an exemplary embodiment of a new and improved readhead 200 constructed in accordance with the present disclosure for use as part of an apparatus for optically inspecting samples of body fluid for medical diagnostic purposes. The read head of FIG. 1 is adapted to perform both fluorescence spectroscopy and reflectance spectroscopy on a body fluid sample.

Figure 2:
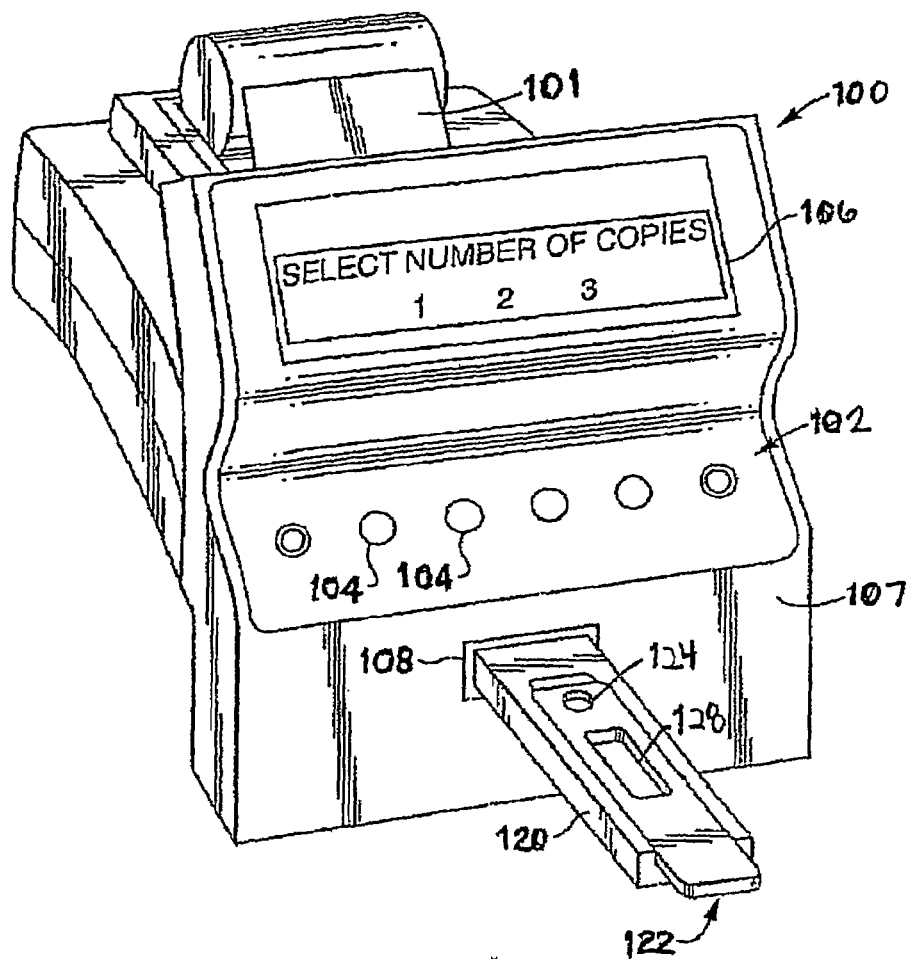
FIG. 2 is a perspective view of an exemplary embodiment of an optical inspection apparatus, which may be used to perform various tests of a body fluid sample.

The new and improved readhead 200 of FIG. 1 can be incorporated into a optical inspection apparatus. Prior to discussing the new and improved readhead 200 of FIG. 1, the apparatus shown in FIGS. 2 through 6 will first be discussed to provide background information on an exemplary embodiment of an optical inspection apparatus. FIG. 2 illustrates a reflectance spectroscope 100, for optically inspecting liquid samples such as body fluid samples. The particular apparatus 100 shown in FIG. 2 is a CLINITEK® 50 Urine Chemistry Analyzer available from Bayer Corporation, Diagnostics Division, of Tarrytown, N.Y. The apparatus 100 is described in greater detail in U.S. Pat. Nos. 5,654,803; 5,877,863; and 5,945,341, which are assigned to the assignee of the present disclosure and incorporated herein by reference.

It should be understood, however, that a new and improved readhead according to the present disclosure can be incorporated in optical inspection machines other than a CLINTEK® 50 Urine Chemistry Analyzer. For example, it is anticipated that a new and improved readhead according to the present disclosure will be incorporated into a CLINITEK STATUS® Chemistry Analyzer available from Bayer Corporation. Aspects of the CLINITEK STATUS® Chemistry Analyzer are disclosed in co-owned and co-pending U.S. patent application Ser. No. 10/821,441, filed on Apr. 9, 2004 and U.S. patent application Ser. No. 10/556,097, which are incorporated herein by reference and which also claim priority to provisional patent application Ser. No. 60/475,288, filed Jun. 3, 2003.

The exemplary inspection apparatus 100 shown in FIG. 2 has an integral keyboard 102 for user input, and a visual display 106 for displaying various messages to a user relating to the operation of the inspection apparatus 100. The inspection apparatus 100 also has a housing 107 with an opening 108 formed therein into which a support tray 120 may be retracted. As shown in FIG. 2, the support tray 120 is adapted to receive a first type of liquid sample carrier or removable insert, which may be in the form of a reagent cassette 122.

The reagent cassette 122 may be a disposable, single-use cassette for doing a pregnancy test, for example, in a conventional manner. The reagent cassette 122 has an opening or well 124 into which a body fluid sample, such as urine, is placed. The interior of the reagent cassette 122 has a reagent strip (not shown) which may react with the body fluid sample placed in the well 124. Depending on the results of the test, the reagent strip may change color (e.g., a colored stripe may appear), which is determinable from viewing the reagent strip through a window 128 of the reagent cassette 122. Although not shown, the support tray 120 may have a calibration chip of a certain color, such as white, disposed in its upper surface to facilitate calibration. A new and improved readhead according to the present disclosure can also be used with a lateral flow immunoassay using a fluorescent particle as a label.

Figure 3:
FIG. 3 is a perspective view of an exemplary embodiment of a reagent strip for use with the apparatus of FIG. 2.

When turned over, the support tray 120 is adapted to receive sample carrier comprising a reagent strip. Referring to FIG. 3, a reagent strip 40 may have a thin, non-reactive substrate 41 on which a number of reagent pads 50 are fixed. Each reagent pad 50 may be composed of a relatively absorbent material impregnated with a respective reagent, each reagent and reagent pad 50 being associated with a particular test to be performed. When urinalysis tests are performed, they may include, for example, a test for leukocytes in the urine, a test of the pH of the urine, a test for blood in the urine, etc. When each reagent pad 50 comes into contact with a urine sample, the pad changes color over a time period, depending on the reagent used and the characteristics of the urine sample. The reagent strip 40 may be, for example, a MULTI-STIX® reagent strip commercially available from Bayer Corporation, Diagnostics Division, of Tarrytown, N.Y.

Referring back to FIG. 2, during an inspection procedure the support tray 120 is moved between an outwardly extended position as shown in FIG. 2 and an optical inspection position in which the tray 120 is retracted inwardly into the housing 107 of the inspection apparatus 100 and into a readhead contained in the housing.

Figure 4:
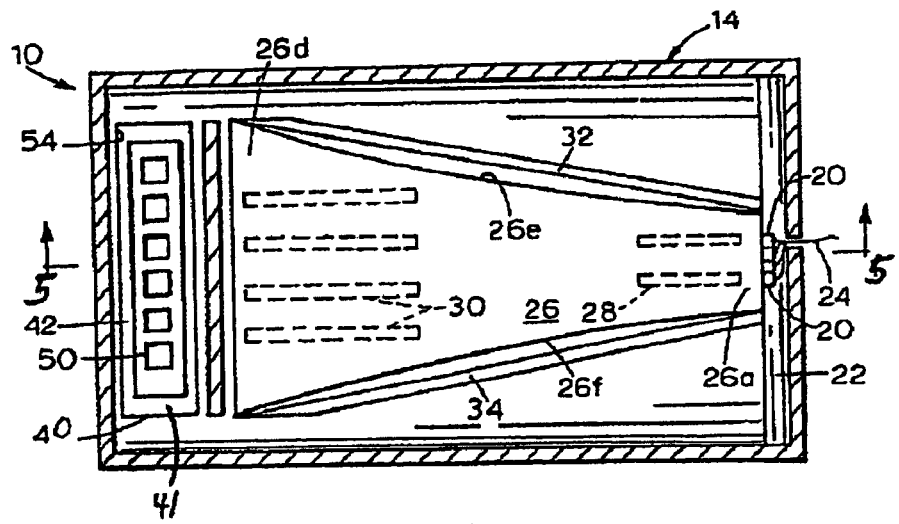
FIG. 4 is a top sectional view of an exemplary embodiment of a readhead for use as part of the optical inspection apparatus of FIG. 2, and which is adapted to allow the apparatus of FIG. 2 to perform reflectance spectroscopy on a body fluid sample.
Figure 5:
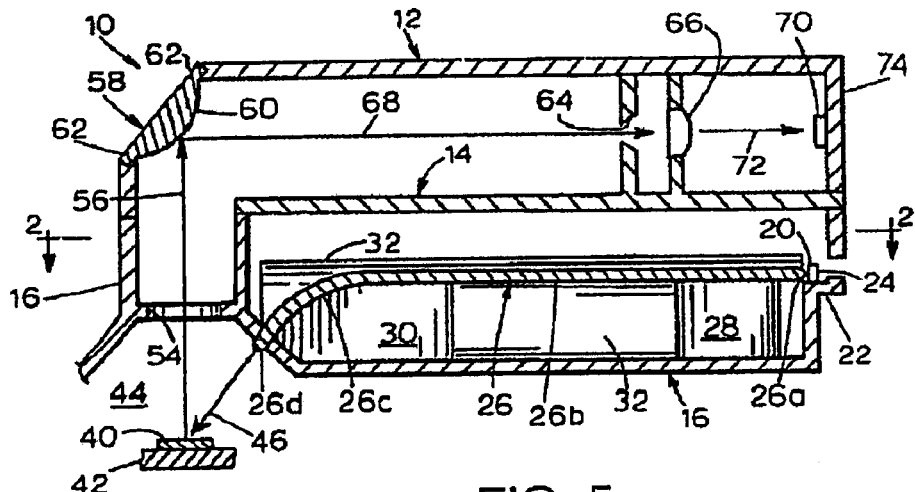
FIG. 5 is a side sectional view of the readhead of FIG. 4.

FIGS. 4 and 5 show an exemplary embodiment of a readhead 10 of the inspection apparatus 100. In the exemplary embodiment shown, the readhead 10 has a housing formed from an upper housing portion 12, a middle housing portion 14, and a lower housing portion 16 which may be connected together in any conventional manner. The housing portions 12, 14, 16 may be injection-molded parts comprising black plastic to substantially absorb any errant light rays that are incident upon the housing.

Light sources in the form of light-emitting diodes (LEDs) 20 are supported on a ledge 22 formed in the lower housing portion 16. Each of the LEDs 20 is designed to emit monochromatic radiation of a different wavelength, corresponding to red light, green light, blue light and infrared. The wavelength of the light emitted may vary from about 400 nanometers (for blue light) to about 1,000 nanometers (for infrared). Each of the LEDs 20 may be selectively turned on and off via a plurality of wires 24 connected between the LEDs 20 and an activation circuit (not shown). The readhead 10 may be provided with additional LEDs providing additional wavelengths. The CLINITEK STATUS® Urine Chemistry Analyzer includes six LEDs, while the CLINITEK® 50 Urine Chemistry Analyzer includes four LEDs.

The LEDs 20 are disposed directly adjacent and in very close proximity with an inlet end 26a of a light guide 26 into which light from the LEDs 20 is radiated. As shown in FIG. 5, the light guide 26 has a relatively long, substantially planar portion 26b and a portion 26c that curves downwardly towards an outlet end 26d of the light guide 26. As shown in FIG. 4, which is a top cross-sectional view of a portion of the readhead 10, the light guide 26 has a pair of curved sides 26e, 26f that diverge outwardly from the inlet end 26a to the outlet end 26d of the light guide 26.

The light guide 26, which may be an injection-molded part composed of clear plastic such as acrylic or polycarbonate, conducts substantially all light that enters its inlet end 26a to its outlet end 26d via total internal reflection. To prevent any internally reflected light from exiting the light guide 26 between its inlet 26a and outlet 26d, the exterior of the light guide 26 could optionally be coated with a highly reflective coating, such as silver.

The light guide 26 is supported within the lower housing portion 16 by a pair of supports 28 disposed beneath the light guide 26 at a point near its inlet end 26a and a plurality of supports 30 disposed beneath the light guide 26 at a point near its outlet end 26d. The supports 28, 30 may be integrally formed with the lower housing portion 16. As shown in FIG. 4, the light guide 26 is positioned between a pair of angled guide walls 32, 34.

As shown in FIG. 5, light is emitted from the outlet end 26d of the light guide 26 towards the reagent strip 40 disposed on a support 42 in an illumination chamber 44, as indicated by an arrow 46. The support 42 is nonmovable relative to the housing portions 12, 14, 16. Light from the reagent strip 40 passes through a rectangular opening 54 formed in the lower housing portion 16, in a direction indicated by an arrow 56, towards a mirror element 58 fixed in the upper left corner of the upper housing portion 12. The mirror element 58 is composed of a cylindrical mirror 60 and a pair of mounting tabs 62 connected to the mirror 60. The mirror element 58, which may be a plastic injection molded part having the curved portion 60 being coated with a highly reflective material, extends approximately the length of the aperture 54 shown in FIG. 5 (the CLINITEK STATUS® Urine Chemistry Analyzer includes a flat mirror). The mirror 60 reflects light that is incident upon it from the reagent strip 40 through a square aperture 64 formed in the middle housing portion 14 and to a lens 66 supported by the middle housing portion 14, as indicated by an arrow 68. One side of the lens 66 has a planar surface and the other side of the lens 66 has a convexly curved (aspheric) surface. Light passing through the lens 66 is transmitted to a light detector array 70, as indicated by an arrow 72.

The detector array 70, which is fixed to a side wall 74 of the upper housing portion 12, may comprise a conventional detector array, such as a TSL 1402 commercially available from Texas Instruments, which is composed of 256 individual light detectors aligned in a single horizontal row, or a Sony ILX511, a 2048 detector array, which is used in the CLINITEK STATUS® Urine Chemistry Analyzer includes.

In operation, only one of the LEDs 20 is illuminated at a time, and the illumination provided by that single LED 20 is sufficient to uniformly illuminate the reagent strip 40 to an extent that allows the detector array 70 to detect enough light from the reagent strip 40 to have the reagent tests described above satisfactorily performed. Each individual light detector in the array 70 senses light from a particular point along the length of the reagent strip 40. For example, to detect light from the lowermost reagent pad 50, a number of the light detectors on the corresponding end of the detector array 70 would be activated. Light from all of the reagent pads 50 could be simultaneously detected by activating all of the detectors in the array 70.

The cross-sectional shape of the mirror 60 is curved so that each light detector in the detector array 70 detects light from a wider portion of the reagent strip 40 than if a mirror having a straight cross-sectional shape were used. However, depending on the particular design of the readhead 10, a straight mirror could be used instead of the cylindrically curved mirror 60. In an alternative design, the mirror element 58 could be omitted, and the detectors 70 could be placed directly above the aperture 54.

Referring to FIG. 4, the light guide 26 is diverging, having a relatively small width at its inlet end 26a and a relatively large width at its outlet end 26d. The fact that the light guide 26 is diverging acts to 1) spread the light from a single one of the LEDs 20 along a relatively large length, corresponding to the length of the outlet end 26d, and 2) cause the light rays emitted by one of the LEDs 20 to be randomized, thus providing more uniform illumination at the target area in which the reagent strip 40 is located, by causing some of the light rays to be internally reflected within the light guide 26 at different angles. With respect to feature 2), it should be understood that in a light guide having diverging side walls, a single light ray may be reflected from the walls at different angles (i.e. at successively shallower angles of incidence with respect to the side walls as the light ray passes from the inlet to the outlet), thus increasing the randomness of the light rays and the uniformity of the illumination.

Figure 6:
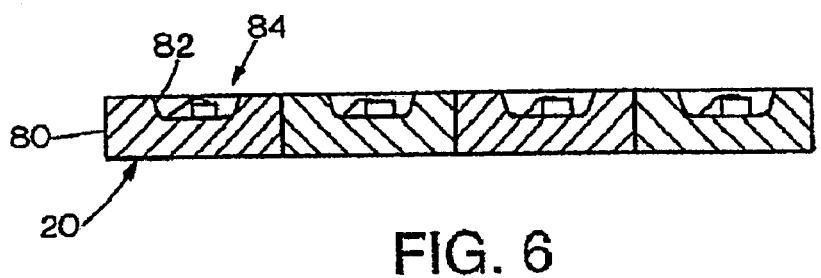
FIG. 6 is a cross-sectional side view of a light-emitting diode array of the readhead of FIG. 4.

In the exemplary embodiment shown, the LEDs 20 comprise lensless LEDs, such as surface-mount LEDs. Conventional LEDs are typically provided with a lens which covers the light-emitting component of the LED, however, a lensless LED acts more of a Lambertian source by exhibiting a much lower degree of directionality. FIG. 6 illustrates the structure of the conventional lensless LEDs 20. Referring to FIG. 6, each LED 20 is shown to generally comprise a substrate 80 having a cavity 82 formed therein, with the light-emitting structure 84 being disposed within the cavity 82 and with no lens covering the cavity 82 or the light-emitting structure 84.

Referring back to FIG. 1, the present disclosure provides a new and improved readhead 200 for use as part of an apparatus (such as the apparatus 100 of FIG. 2) for optically inspecting samples of body fluid for medical diagnostic purposes. The read head 200 of FIG. 1 is similar to the readhead 10 of FIGS. 4 and 5 such that similar elements have the same reference numeral preceded by a "2". The read head 200 of FIG. 1 however is adapted to perform fluorescence spectroscopy, in addition to reflectance spectroscopy, on a body fluid sample.

In FIG. 1 only an end portion of the readhead 200 is shown. Although not shown in FIG. 1, the readhead 200 also includes LEDs, a lens and a detector array, similar to the readhead 10 of FIGS. 4 and 5. In addition to the LEDs, however, the readhead 200 of FIG. 1 further includes an ultraviolet light source chamber 300 containing an ultraviolet light source 302 and having an opening 304 for directing light from the ultraviolet light source 302 into the illumination chamber 244 of the readhead 200. As shown, the interior of the chamber 300 may be lined with metal foil 306 to protect the plastic walls of the chamber from ultraviolet light degradation. The readhead 200 also includes an ultraviolet filter 308 in the light path 256 to prevent an excitation wavelength of the light source 302 from being detected by the detector array, so that the detector array will only detect an emission wavelength produced by the pads 50 of the reagent strip 40.

Many substances will fluoresce (re-emit energy at a higher wavelength) when exposed to ultraviolet light. During use of the readhead 200 of the present disclosure, ultraviolet excitation light from the light source 302 is directed against the pads 50 of the reagent strip 40, as illustrated by arrow 310. Emission light from the pads 50 of the reagent strip 40 then travels through the ultraviolet filter 308 in the light path 256, is reflected off the mirror 260 and directed along the light path 268 to the detector array. Determining the wavelength and intensity of emissive light received by the detector array can be used to determine properties of the sample being excited with the light source 302. For instance, the wavelength and intensity of emissive light can be used to determine the amount of glucose in a blood sample. U.S. Pat. No. 6,232,609 to Snyder et al., for example, shows an apparatus for glucose monitoring that uses ultraviolet excitation and monitors the wavelength and intensity of emissive light to monitor glucose levels.

According to one exemplary embodiment of the present disclosure, the detector array monitors the return light and generates electrical signals indicative of the intensity of return light associated with glucose concentration distinguishing characteristics of the emission light. A processor connected to the detector array processes the electrical signals, using a predictive model, to determine the concentration of glucose in the sample. Suitable examples of predictive models are shown in U.S. Pat. No. 6,232,609 to Snyder et al.

According to another exemplary embodiment of the disclosure, the light source 302 comprises a black fluorescent lamp having a line output at 364 nanometers, 405 nanometers, and 436 nanometers, and a broadband output from 330-385 nanometers. Alternatively, the light source may comprise an ultraviolet LED positioned in the ultraviolet light source chamber 300 or adjacent to the other LEDs 20 at the input end of the light guide 26. The ultraviolet LED may have an output of 370 nanometers or 400 nanometers, for example. The light guide 26 for an ultraviolet LED is made of glass or quartz. In addition, a high intensity green LED can be used to trigger fluorescence, and can be used with suitable filters. It should be anticipated that future LEDs will cover a wider range of UV wavelengths and that more fluorescent dyes or markers will also be developed.

Numerous further modifications and alternative embodiments of the disclosure will be apparent to those skilled in the art in view of the foregoing description. This description is to be construed as illustrative only, and is for the purpose of teaching those skilled in the art the best mode of carrying out the disclosure. The details of the structure and method may be varied substantially without departing from the spirit of the disclosure, and the exclusive use of all modifications which come within the scope of the appended claims is reserved.

What is claimed is:

1. A readhead for a diagnostic instrument for illuminating a sample carrier and receiving light from the sample carrier, the readhead comprising:

a housing adapted to be incorporated in the diagnostic instrument and including an illumination chamber for receiving a sample carrier;

an array of reflectance light sources mounted within the housing in a fixed position relative to the illumination chamber, and including a first light-emitting diode for emitting substantially monochromatic light of a first wavelength and a second light-emitting diode for emitting substantially monochromatic light of a second wavelength substantially different from the first wavelength;

a light guide mounted in the housing to receive light from each of the light-emitting diodes, for conveying, when only one of the light-emitting diodes is illuminated, substantially all of the light from the one light-emitting diode to the illumination chamber so that the illumination chamber is illuminated substantially uniformly;

a light detector coupled to receive light from the illumination chamber;

a fluorescence excitation light source positioned in the housing and positioned to direct excitation light of a predetermined wavelength to the illumination chamber; and a light filter positioned between the illumination chamber and the light detector and adapted to prevent passage therethrough of the excitation light from the fluorescence excitation light source but allow passage of emissive light from a sample carrier in the illumination chamber having a wavelength different from the predetermined wavelength of the excitation light.

2. A readhead as defined in claim 1 wherein the fluorescence excitation light source comprises an ultraviolet light source.

3. A readhead as defined in claim 2 wherein the ultraviolet light source comprises a black fluorescent lamp having a line output at 364 nanometers, 405 nanometers, and 436 nanometers, and a broadband output from 330-385 nanometers.

4. A readhead as defined in claim 3 wherein the black fluorescent lamp is positioned in an ultraviolet light source chamber of the housing, and the ultraviolet light source chamber is lined with metal foil.

5. A readhead as defined in claim 1 wherein a mirror is positioned between the light detector and the light filter.

6. A readhead as defined in claim 1 wherein a lens is positioned between the light detector and the light filter and adapted to focus light on the light detector.

7. A diagnostic instrument including a readhead as defined in claim 1 and further comprising a processor connected to the light detector and programmed to process electrical signals from the light detector to determine a physical property of a sample on a sample carrier received in the illumination chamber of the readhead.

8. A diagnostic instrument as defined in claim 7 wherein the processor is programmed to use a predictive model to determine the physical property.

9. A readhead as defined in claim 1 wherein the light guide comprises a diverging light guide having a relatively small width at a point adjacent an inlet of the diverging light guide and a relatively large width at a point adjacent an outlet of the diverging light guide.

10. A readhead for a diagnostic instrument for illuminating a sample carrier and receiving light from the sample carrier, the readhead comprising:
a housing adapted to be incorporated in the diagnostic instrument and adapted to receive and support a sample carrier;
a reflectance light source comprising a light-emitting diode mounted within the housing in a fixed position relative to the sample carrier;
a diverging light guide, mounted in the housing to receive light from the light-emitting diode and adapted to convey substantially all of the light from the light-emitting diode to the sample carrier so that the sample carrier is illuminated substantially uniformly, the diverging light guide having a relatively small width at a point adjacent an inlet of the diverging light guide and a relatively large width at a point adjacent an outlet of the diverging light guide;
a light detector coupled to receive light from the sample carrier;
a fluorescence excitation light source for directing excitation light of a predetermined wavelength to the sample carrier; and
a light filter positioned between the sample carrier and the light detector and adapted to prevent passage therethrough of the excitation light from the fluorescence excitation light source but allow passage of emissive light from the sample carrier having a wavelength different from the predetermined wavelength of the excitation light.

11. A readhead as defined in claim 10 wherein the fluorescence excitation light source comprises an ultraviolet light source.

12. A readhead as defined in claim 11 wherein the ultraviolet light source comprises a black fluorescent lamp having a line output at 364 nanometers, 405 nanometers, and 436 nanometers, and a broadband output from 330-385 nanometers.

13. A readhead as defined in claim 10 wherein a mirror is positioned between the light detector, and the light filter.

14. A readhead as defined in claim 10 wherein a lens is positioned between the light detector and the light filter and adapted to focus light on the light detector.

15. A diagnostic instrument including a readhead as defined in claim 10 and further comprising a processor connected to the light detector and programmed to process electrical signals from the light detector to determine a physical property of a sample on a sample carrier received in the readhead.

16. A diagnostic instrument as defined in claim 15 wherein the processor is programmed to use a predictive model to determine the physical property.

17. A readhead for a diagnostic instrument for illuminating a sample carrier and receiving light from the sample carrier, the readhead comprising:
a housing adapted to be incorporated in the diagnostic instrument and including an illumination chamber for receiving a sample carrier;
a reflectance light source comprising a lensless light-emitting diode mounted within the housing in a fixed position relative to the illumination chamber;
a light guide, mounted in a fixed position relative to the lensless light-emitting diode, for conveying light from the lensless light-emitting diode to a sample carrier in the illumination chamber;
a light detector coupled to receive light from the sample carrier;
a fluorescence excitation light source positioned in the housing for directing excitation light of a predetermined wavelength to the illumination chamber; and
a light filter positioned between the illumination chamber and the light detector and adapted to prevent passage therethrough of the excitation light from the fluorescence excitation light source but allow passage of emissive light from a sample carrier in the illumination chamber having a wavelength different from the predetermined wavelength of the excitation light.

18. A readhead as defined in claim 17 wherein the fluorescence excitation light source comprises an ultraviolet light source.

19. A readhead as defined in claim 18 wherein the ultraviolet light source comprises a black fluorescent lamp having a line output at 364 nanometers, 405 nanometers, and 436 nanometers, and a broadband output from 330-385 nanometers.

20. A readhead as defined in claim 18 wherein the ultraviolet light source is positioned in a chamber of the housing, lined with metal foil.

21. A readhead as defined in claim 17 wherein a mirror is positioned between the light detector and the light filter.

22. A readhead as defined in claim 17 wherein a lens is positioned between the light detector and the light filter and adapted to focus light on the light detector.

23. A diagnostic instrument including a readhead as defined in claim 17 and further comprising a processor connected to the light detector and programmed to process electrical signals from the light detector to determine a physical property of a sample on a sample carrier received in the illumination chamber of the readhead.

24. A diagnostic instrument as defined in claim 23 wherein the processor is programmed to use a predictive model to determine the physical property.

25. A readhead as defined in claim 17 wherein the light guide comprises a diverging light guide having a relatively small width at a point adjacent an inlet of the diverging light guide and a relatively large width at a point adjacent an outlet of the diverging light guide.

26. A diagnostic instrument as defined in claim 23 wherein the physical property comprises a glucose concentration.

27. A diagnostic instrument as defined in claim 15 wherein the physical property comprises a glucose concentration.

28. A diagnostic instrument as defined in claim 7 wherein the physical property comprises a glucose concentration.

29. A readhead as defined in claim 18 wherein the ultraviolet light source comprises a light-emitting diode.

30. A readhead as defined in claim 29 wherein the light-emitting diode comprises a high intensity green light-emitting diode.

31. A readhead as defined in claim 29 wherein the ultraviolet light-emitting diode is positioned next to the reflectance light source and the light guide comprises glass or quartz.

32. A readhead as defined in claim 11 wherein the ultraviolet light source comprises a light-emitting diode.

33. A readhead as defined in claim 32 wherein the light-emitting diode comprises a high intensity green light-emitting diode.

34. A readhead as defined in claim 32 wherein the ultraviolet light-emitting diode is positioned next to the reflectance light source and the light guide comprises glass or quartz.

35. A readhead as defined in claim 2 wherein the ultraviolet light source comprises a light-emitting diode.

36. A readhead as defined in claim 35 wherein the light-emitting diode comprises a high intensity green light-emitting diode.

37. A readhead as defined in claim 35 wherein the ultraviolet light-emitting diode is positioned next to the reflectance light source and the light guide comprises glass or quartz.

* * * * *